(12) United States Patent
Bauer et al.

(10) Patent No.: US 8,348,852 B2
(45) Date of Patent: Jan. 8, 2013

(54) HEART-ACTIVITY SOUND MONITORING

(75) Inventors: Peter T. Bauer, West Linn, OR (US);
Peter M. Galen, Portland, OR (US);
Martin Baumer, Carlton, OR (US)

(73) Assignee: Inovise Medical, Inc., Beaverton, OR (US)

( * ) Notice: Subject to any disclaimer, the term of this patent is extended or adjusted under 35 U.S.C. 154(b) by 360 days.

(21) Appl. No.: 12/315,165

(22) Filed: Nov. 25, 2008

(65) Prior Publication Data
US 2009/0227886 A1 Sep. 10, 2009

Related U.S. Application Data

(60) Provisional application No. 61/068,353, filed on Mar. 6, 2008.

(51) Int. Cl.
*A61B 5/02* (2006.01)
(52) U.S. Cl. .......... 600/508; 600/509; 600/528
(58) Field of Classification Search .......... 600/508–509, 600/528
See application file for complete search history.

(56) References Cited

U.S. PATENT DOCUMENTS

| | | | |
|---|---|---|---|
| 5,392,780 A | 2/1995 | Ogino et al. |
| 5,758,654 A | 6/1998 | Burton-Krahn et al. |
| 7,039,538 B2 | 5/2006 | Baker, Jr. |
| 7,074,195 B2 | 7/2006 | Nelson et al. |
| 7,096,060 B2 | 8/2006 | Arand et al. |
| 7,113,820 B2 | 9/2006 | Schlegel et al. |
| 7,171,269 B1 | 1/2007 | Addison et al. |
| 7,174,203 B2 | 2/2007 | Arand et al. |
| 7,225,021 B1 | 5/2007 | Park et al. |
| 7,302,290 B2 | 11/2007 | Bauer |
| 7,424,321 B2 | 9/2008 | Wariar et al. |
| 7,431,699 B2 | 10/2008 | Siejko et al. |
| 7,559,903 B2 | 7/2009 | Moussavi et al. |
| 7,819,814 B2 | 10/2010 | Gavriely et al. |
| 8,105,241 B2 | 1/2012 | Nelson et al. |
| 8,137,283 B2 | 3/2012 | Syeda-Mahmood et al. |
| 2002/0188329 A1 | 12/2002 | Struble |
| 2003/0187337 A1 | 10/2003 | Tarassenko et al. |
| 2004/0127792 A1 | 7/2004 | Siejko et al. |
| 2004/0230105 A1 | 11/2004 | Geva et al. |
| 2005/0027323 A1 | 2/2005 | Mulligan et al. |
| 2005/0222515 A1 | 10/2005 | Polyshchuk et al. |
| 2006/0155202 A1 | 7/2006 | Arand et al. |
| 2007/0038137 A1 | 2/2007 | Arand et al. |

(Continued)

FOREIGN PATENT DOCUMENTS
CA 1256507 6/1989

OTHER PUBLICATIONS

International Search Report, Serial No. PCT/US10/055696, dated Dec. 23, 2010, 13 pages total.

(Continued)

*Primary Examiner* — Nicole F Lavert
(74) *Attorney, Agent, or Firm* — Jon M. Dickinson; Robert D. Varitz

(57) ABSTRACT

A method for acquiring, externally or internally, for utility purposes a subject's anatomical heart-sound information including (a) for a selected time period, applying continuous, near-sensor-mechanical-resonance, vibratory stimulation to an acoustic sensor placed on or within the subject's anatomy, and (b) during that time period, detecting, as direct indications of heart sounds, changes in the sensor's physical resonance properties produced by heart sounds arriving at the sensor.

5 Claims, 1 Drawing Sheet

U.S. PATENT DOCUMENTS

| | | | |
|---|---|---|---|
| 2007/0055151 A1 | 3/2007 | Shertukde et al. | |
| 2007/0191725 A1 | 8/2007 | Nelson | |
| 2008/0021510 A1* | 1/2008 | Mi et al. | 607/36 |
| 2008/0177191 A1* | 7/2008 | Patangay et al. | 600/509 |
| 2008/0255465 A1 | 10/2008 | Nelson | |
| 2009/0112107 A1 | 4/2009 | Nelson et al. | |
| 2009/0112108 A1 | 4/2009 | Nelson et al. | |
| 2009/0165559 A1* | 7/2009 | Lec | 73/579 |
| 2010/0094148 A1 | 4/2010 | Bauer et al. | |

OTHER PUBLICATIONS

USPTO Office Action, U.S. Appl. No. 12/315,165, dated Nov. 12, 2010, 9 pages total.

USPTO Office Action, U.S. Appl. No. 11/264,328, dated May 9, 2008, 7 pages total.

USPTO Office Action, U.S. Appl. No. 11/264,328, dated Oct. 16, 2008, 8 pages total.

* cited by examiner

HEART-ACTIVITY SOUND MONITORING

CROSS REFERENCE TO RELATED APPLICATION

This Application claims priority to U.S. Provisional Patent Application Ser. No. 61/068,353, filed Mar. 6, 2008, for "Heart Activity Sound Monitoring", the contents of which are incorporated hereinto by reference.

BACKGROUND AND SUMMARY OF THE INVENTION

This invention relates to methodology enabling, selectively, external, or implantable, active detection of anatomical acoustic heart-sound information. Specifically it pertains to an active method based upon: (a) utilizing a wave-generator-driven stimulator, or actuator, to stimulate mechanically, and thereby vibrate, an acoustic sensor (designed especially for capturing heart sounds, and placed externally on, or within, the anatomy) at a frequency close to the sensor's nominal, characteristic, mechanical resonance frequency; (b) observing variations in this characteristic mechanical frequency that occur over time in the sensor as a consequence of the mechanical impinging of acoustic waves, and particularly heart-sound waves; and then (c) effectively recognizing that these time-based variations may accurately and thoughtfully be interpreted as being representative of occurring anatomical acoustical activity, and in particular, heart sounds.

With this unique approach, acoustic sensitivity is very high, and so also is signal-to-noise ratio. For primary illustration purposes herein, one preferred and best-mode manner of practicing the methodology of the invention is described chiefly in the "external" placement and operational setting, wherein it has been found to offer exemplary performance.

Regarding the prior-art setting of the present invention, external electronic and acoustic transducers have been used, and are well known, to detect chest wall vibrations caused by heart sounds. Generally, passive transducer systems have been employed to detect such vibrations. These transducers typically employ any of microphones embedded in a generally bell-shaped (or other) housing, accelerometer techniques using piezoelectric and/or resistive transducers, or fully integrated medical event-monitoring systems (MEMS) devices. The techniques used in conjunction with such known devices and techniques are often limited because of less than satisfactory sensitivity and signal-to-noise-ratio behaviors associated with the transducers.

In general terms, overall prior art data-collection practice for evaluating, and even for "driving" real-time therapy and treatment of, cardio-function conditions of a subject's heart involves principally the gathering of two, different categories of data—electrical, and acoustical. For example, ECG-electrical information for diagnostic purposes, such as for providing "synchronizing" fiducial markers to understand when certain heart-activity events are occurring, as well as for other important reasons, is very well known. Known also is the fact that collected, heart-activity-produced sound (acoustical) information, i.e., heart sounds, provides extremely useful diagnostic data. With respect to the matter of heart-sound collection, since the early days of phonocardiography, the importance of gathering the so-called S1, S2, S3 and S4 heart sounds has been clearly recognized. Information-gathering practice over the years has demonstrated how electrical ECG signals and the important, heart-produced S1, S2, S3 and S4 heart-sound signals may be correlated in different ways to produce accurate, useful diagnostic information.

In all of this background, heart-related, signal-collection practice, a continuing challenge remains. It relates to achieving the clear, accurate and plainly identifiable gathering of heart sounds. The present invention focuses its attention on this issue, and does so with a featured, special and unique, "active", rather than purely passive, methodology which may be practiced either externally, or implantably, as, for example, in association with an implanted pacemaker.

In accordance with a preferred, and best-mode, implementation of the invention, what is proposed is a method for acquiring, for various utility purposes, such as the display-presentation of accurate heart-sound data, or the establishment of a patient-treatment protocol, among others, a subject's anatomical heart-sound information involving the following basic steps:

(a) utilizing a wave-generator-driven stimulator, or actuator, to stimulate mechanically, and vibrate, an acoustic sensor (placed on or within the anatomy) at a frequency close to the sensor's nominal, characteristic, mechanical resonance frequency;

(b) observing variations in this characteristic mechanical frequency that occur over time in the sensor as a consequence of the mechanical impinging of acoustic heart-sound waves; and then (c) effectively recognizing that these time-based variations may accurately be interpreted as being representative of occurring heart sounds.

In a more specific sense, the invention furnishes a unique, active method for acquiring a subject's anatomical heart-sound information which is useful in performing a cardio investigation, and in producing a related utility output, such as the ones briefly mentioned above, involving that subject. This method more specifically includes the steps of:

(a) placing on or within the subject's anatomy at a selected anatomical site an acoustic sensor having the form of an acoustical-to-electrical-output transducer possessing a known, characteristic mechanical resonance frequency;

(b) using a wave generator having an electrical output, stimulating (actuating) the transducer via an actuator to vibrate the transducer mechanically at a frequency which is close to its characteristic resonance frequency;

(c) coupling to a frequency and phase comparator the electrical outputs of the transducer and of the wave generator;

(d) observing over time any time-based differences which exist between the two, thus-compared outputs;

(e) interpreting such observed differences as being representations of the subject's heart sounds; and (f) from such interpreted differences, producing a utility output associated with the subject.

The transducer and the actuator/stimulator may either be directly mechanically integrated in a unified structure, or alternatively, may be non-integrated, but used during practice of the method of the invention in what might be referred to as being in close "mechanical communication", i.e., in close proximity to one another, as through closely adjacent contact with a subject's anatomy. While certain modest structural suggestions are made herein, it should be understood that the present invention is not concerned with the particular structural configuration(s) chosen for the transducer/actuator component, or components, and thus no special details of either are elaborated herein. Those generally skilled in the relevant art will know how to configure and implement such structures in conventional manners, both for external and internal (implanted) applications.

Preferably, the transducer is selected to possess a natural mechanical resonance frequency which lies within the known range of heart-sound frequencies (about 5-Hz to about 110-

Hz). We have found that a good range to consider for this resonance frequency is about 10-Hz to about 110-Hz, and we illustrate the invention herein with an excellent choice of about 30-Hz. With this natural mechanical resonance frequency chosen for the transducer, a good, and very practical stimulation/vibration frequency has been found to be about 15-Hz. This turns out to be a frequency which resides naturally toward one side of the peak natural resonance frequency response curve, or graph, of the transducer, and "lies" on that curve at a point which is approximately centered on, and between the opposite ends of, one of the two, well-recognized, substantially linear portions of the response-amplitude curve that are disposed on laterally opposite sides of the "central" natural resonance frequency.

These and other important features and advantages offered by the methodology of the present invention will become more fully apparent as the description now follows below is read in conjunction with the accompanying drawings.

DESCRIPTION OF THE DRAWINGS

FIG. 1 is organized and presented in a manner which permits illustrated discussion of several preferred practice versions or modifications of the invention, including both external and implanted (in a pacemaker) applications.

DETAILED DESCRIPTION OF THE INVENTION

Figure 1:
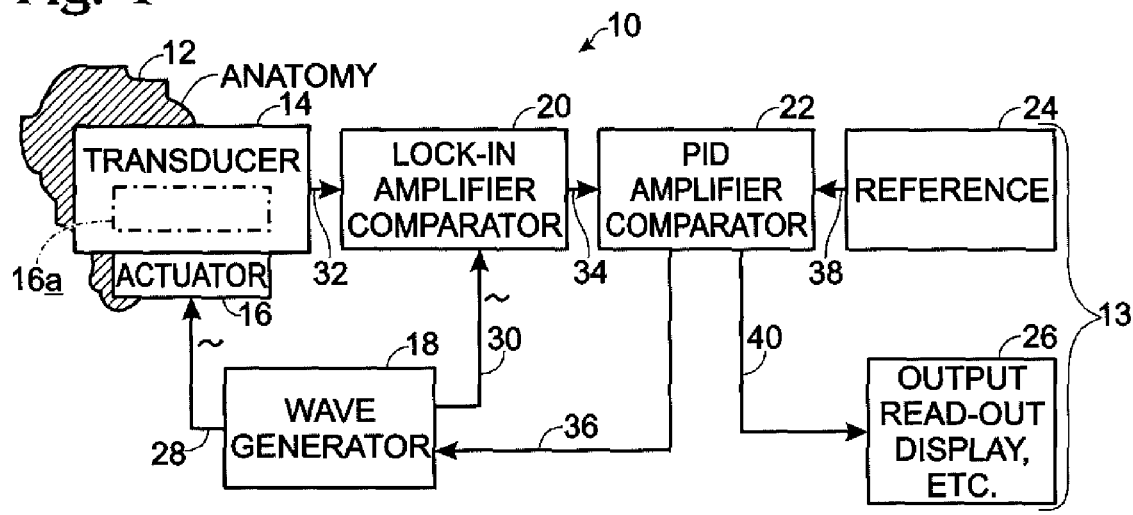
FIG. 1 is a block/schematic diagram of the methodology of the present invention, and also of a system organization which is useful for practicing this methodology. As will be seen.

Turning now to the drawings, and referring first of all to FIG. 1, indicated generally at 10, in block/schematic form, are both the preferred and best-mode versions, or embodiments, of the methodology of the present invention, and a relevant system organization of electrical circuit components which may be assembled as illustrated to carry out and perform the methodology of the invention. Indicated generally at 12 is a fragmentary portion of a subject's anatomy, such as a portion of the chest, with respect to which the methodology of the invention is to be practiced in accordance with what is shown in FIG. 1. Description of the invention will proceed principally and initially in the context of an external application wherein the various circuitry elements/components shown in FIG. 1 are all disposed outside anatomy 12. A bracket 13 which appears at the right side of the figure represents aspects of an internal/implanted modified-invention-form application wherein, for example, this bracket specifically represents an implanted pacemaker wherein the same, just-mentioned circuitry elements are present within anatomy 12 in the pacemaker structure, per se.

Continuing, then, with a representative, external-application description, included further in what is shown in FIG. 1 are several, solid-outline blocks 14, 16, 18, 20, 22, 24 and 26. Different, operative, signal-flow and communication connections, represented by arrow-headed connection, or communication, lines, variously interconnect these blocks, as shown at 28, 30, 32, 34, 36, 38, and 40. Also appearing in FIG. 1, within block 14, is a dash-dot-outline block 16a, the nature of which involves another modified form of the invention. Block 16a will be explained shortly.

As can be seen, each of the several blocks which is pictured in solid outline in FIG. 1 is word-labeled to indicate both its function, and to some extent its structure.

Block 14 represents an acoustic sensor in the form of what is referred to herein as an acoustic-to-electrical transducer which may take any one of a different number of suitable conventional forms, such as the form of a generally bell-shaped structure (not specifically shown) having a generally circular footprint which seats appropriately against the illustrated, selected site in the anatomy portion of the chest wall shown at 12. This transducer is equipped with an appropriate device of any nature, such as a microphone like device, a piezoelectric device, etc. which is designed nominally to respond well to anatomical acoustic sounds, and most preferably to each of the four, above-mentioned, recognized, important heart sounds, S1, S2, S3 and S4, and to produce, on and over communication line in 32, an electrical signal output which has a waveform that is characteristic of whatever sounds are collected and noted by the transducer. Transducer 14 herein has a known, natural, characteristic resonance frequency of about 30-Hz which, as was mentioned earlier, lies within the known frequency range of the four, above-identified, important heart sounds.

Block 16 herein represents an energizable actuator or stimulator which may be energized, via signal line 28, from block 18—a conventional electrical wave generator. Actuator 16, as illustrated in solid-outline block form herein, is represented in a condition wherein it is not integrated with transducer 14, but is being used, in the particular practice of the invention so far described and illustrated in FIG. 1, in what is referred to herein as being an operatively mechanically communicative relationship with the transducer, preferably in very close proximity on anatomy 12 to the transducer. Where, as an illustration, transducer 14 is a bell-shaped, circular-footprint device, actuator 16 might usefully be a generally circular, transducer-circumsurrounding, piezoelectric, ceramic ring-like structure. We will assume for the purposes of further, present discussion herein, that these respective configurations and natures of the transducer and actuator are fact.

It is intended that operation of wave generator 18, in accordance with practice of the invention, will stimulate actuator 16 by energizing it, which action will thereby stimulate and vibrate the transducer at whatever is the stimulation frequency employed by wave generator 18 to energize the actuator. Generator 18 herein is nominally "referenced", effectively by block 24, through block 22 and line 36 (as will be explained), to "operate" at a frequency of about 15-Hz. More will be spoken of this shortly.

Signal line 40 is electrically the same as line 36, and functions to send to block 26 exactly the same signal voltage, whatever it is at the moment. Block 26 functions to create what is referred to herein as a utility output which may take one or more of various useful forms, such as a display (as will be explained shortly) of heart-sound waves, a control signal for initiating/performing some form of cardio-function therapy, such as adjusting the operation of a pacemaker, and other things which will readily come to the minds of those skilled in the relevant art.

Figure 2:
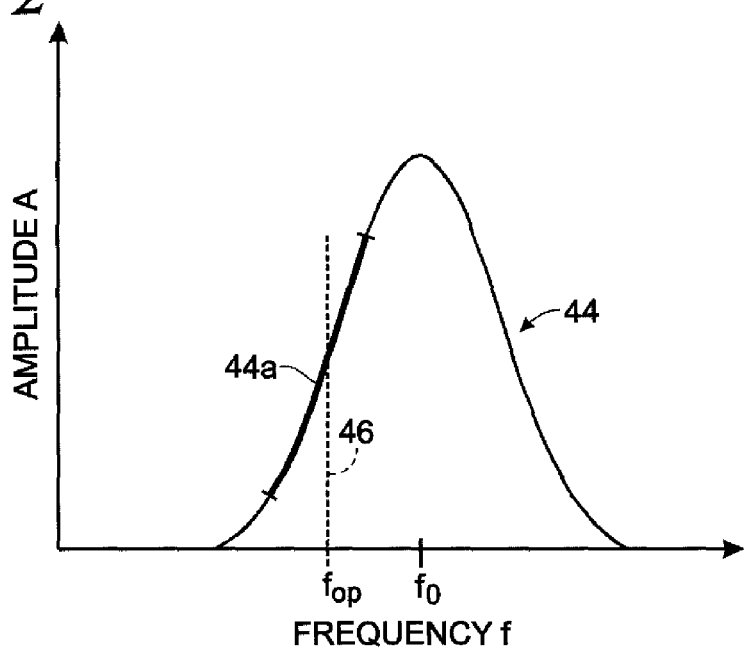
FIG. 2 is a graph depicting the characteristic relationship (the above-mentioned curve) between frequency and mechanical resonance response amplitude associated with a sensor/transducer which is employed preferably in the practice of the invention.

Turning attention for a moment to FIG. 2, here there is illustrated, generally at 44, a curve, or a graph, which represents the mechanical natural frequency response characteristic of transducer 14. Response amplitude A is represented by the vertical axis in FIG. 2, and frequency f is represented on the horizontal axis in this figure.

The central natural resonance frequency of transducer 14 is represented in FIG. 2 on the horizontal axis therein at $f_0$. The illustrated resonance amplitude response characteristic, which is very typical in form, and well understood by those generally skilled in the art, has a somewhat bell-shaped curvature, with opposite lateral sides distributed on the opposite side of the central resonance frequency, and with each side including a generally linear region, such as the linear region shown by a darkened portion 44a of curve 44 located toward the left side in FIG. 2. In general terms, the nominal frequency at which wave generator 18 stimulates and excites actuator 16, thereby similarly stimulating and vibrating transducer 14 is represented by a vertical, dashed line 46 in FIG. 2, and is labeled on the horizontal axis in this figure with the designator $f_{op}$. One can see in FIG. 2 that this stimulation frequency intersects linear portion 44a approximately centrally between that portion's opposite ends.

As was indicated earlier herein, transducer 14 has been selected to have a central natural resonance frequency of about 30-Hz, and that the stimulation operating frequency of wave generator 18, under this circumstance, has been chosen to be about 15-Hz. Accordingly, axis mark $f_0$ in FIG. 2 indicates the frequency 30-Hz, and axis mark $f_{op}$ in this figure indicates the frequency 15-Hz.

Blocks 20 and 22 in FIG. 1 respectively represent the structures and functionalities of a Lock-in Amplifier Comparator, and a PID (proportional integral derivative) Amplifier Comparator, which are conventional structures that perform conventional functions, and which are well understood by those generally skilled in the art. Nominally, i.e., in the absence of any anatomical acoustic sounds detected by transducer 14, in-phase electrical output signals from wave generator 18 are supplied at the frequency of 15-Hz via communication line 28 to actuator 16, and via communication line 30 to one of two, provided comparator inputs in block 20, the lock-in amplifier comparator. Electrical output signals, of whatever nature, from transducer 14 are supplied to the other comparator input in block 20 via communication line 32. The electrical "comparison" output of block 20 (shortly to be explained) is coupled to one of two, provided comparator inputs in PID Amplifier Comparator block 22 by communication line 34, and what will be referred to herein as a wave-generator frequency-control signal (which will also shortly be explained) is supplied by block 22 via communication line 36 to the wave generator. This very same signal, as was mentioned above, is furnished by signal line 40 to utility output block 26.

Nominally, block 24 functions as a DC Reference voltage block which supplies a DC reference voltage via signal line 38 to the other comparator input in comparator block 22. This arrangement results in Reference block 24 effectively, nominally, through block 22, and signal line 36, establishing the mentioned 15-Hz operating frequency for output from wave generator 18 via signal line 28 to actuator 16, and via signal line 30, to the lock-in amplifier comparator represented by block 20. These so-called nominal conditions are the conditions existing in the absence of any anatomical acoustic activity (waves) detected by transducer 14.

By way of an operation which will shortly be described, signal line 40 couples an appropriate output control signal from block 22 to block 26. Block 26 represents the generation and or production by the methodology of the present invention of what is referred to as a utility output. This utility output may take the form of an appropriate output readout provided on a display screen to inform an operator of the methodology of information acquired from a subject, may be utilized to perform certain tasks that are related to managing the hemodynamic condition of the subject whose data is being collected, and otherwise may be employed for the production of an appropriate therapy or treatment protocol for a particular subject.

One aspect to note in relation to what has just been described in relation to FIG. 1 is that transducer 14, actuator 16, wave generator 18, lock-in amplifier comparator 20, and referenced PID amplifier comparator 22 are organized in a closed, negative feedback circuit or loop which plays an important role, as will become apparent, in the practice of the methodology of the invention.

Explaining now the operation of what is shown and has just been described in relation to FIG. 1, and starting this description under circumstances where no anatomical acoustic waves, such as heart sounds, are being detected by transducer 14, wave generator 18, through adapter 16, stimulates and vibrates the transducer at the frequency of 15-Hz. Transducer 14 responds to this vibratory stimulation to produce an electrical output signal having an amplitude which is related to the amplitude of its mechanical frequency response curve at the location pictured in FIG. 2 where dashed line 46 intersects linear portion 44a in the curve 44. This signal is in-phase with the vibratory stimulation signal then being sent by wave generator 18.

The transducers' electrical output signal is supplied to amplifier comparator 20 via signal line 32, is compared in comparator 20 with the same-frequency, and in-phase, signal supplied by wave generator 18 to the amplifier comparator 20 via signal line 30, and the result is that comparator 20 produces, on signal line 34, some level of a DC voltage. This line-34 DC voltage, when compared in PID amplifier comparator 22 with the DC reference voltage supplied from reference block 24 over line 38, produces some predetermined DC voltage on line 36 which, when applied as shown to wave generator 18, functions to maintain the operating frequency of the wave generator substantially constant at 15-Hz.

Those skilled in the art will recognize that there are many levels of appropriate DC voltages, of the characters and functionalities just mentioned, which may be established in the "nominal" operating pattern that has just been described. Under these "nominal" conditions, there exists in the arrangement shown at 10 in FIG. 1, a steady-state condition having the features just described. This condition, of course, is largely a fiction, disappearing just as soon as transducer 14 is positioned to react to anatomical acoustic behavior, but the description of the "nominal" condition sets an informative stage for understanding what takes place when such a reaction begins occurring.

This "nominal" situation thus changes immediately upon receipt by transducer 14 of impacting mechanical sound waves, such as heart-sound waves, coming from anatomy 12. When this occurs, these impacting sound waves effectively change and alter the characteristic resonance frequency of the transducer, causing the transducer's resonance-frequency response curve which is pictured in FIG. 2 to shift to the left or to the right, and in fact continuously laterally back and forth in that figure relative to dashed line 46 in accordance with the amplitude and phase of the impacting sound waves.

This responsive change in the behavior of transducer 14 produces a time-based voltage variation in the transducer's electrical output signal which appears on signal line 32, and thus at one of the two, earlier-mentioned comparator inputs present in amplifier comparator 20. In amplifier comparator 20, this situation produces an immediate comparison with the signal being provided thereto from the wave generator over signal line 30, and what then results is a time-based voltage shift in the voltage level present on signal line 34 which is supplied to one of the earlier-mentioned comparator inputs provided in PID amplifier comparator 22.

A consequence of this operation, of course, is that the time-based voltage changes, or variations, arriving from transducer 14, which variations then become distinguished by comparison in block 20 with the voltage waveform arriving from the wave generator, produce on signal line 34 a time-varying voltage whose variations directly follow the waveform(s) of the acoustic information arriving at the transducer. In other words, what now appears on line 34 is a signal which directly follows, and thereby directly indicates, transducer-received anatomical acoustic sounds—the S1, S2, S3 and S4 sounds Supplied, then, by block 20 to amplifier comparator block 22, over signal line 34, to become compared in block 22 with the fixed DC reference voltage supplied over line 38 by block 24 to block 22, is this time-varying voltage signal just described on line 34. The comparison which then takes place in block 22 produces, on each of signal lines 36, 40, a common, time-based varying voltage signal which also, and very clearly, directly follows the waveform(s) of the acoustic S1, S2, S3 and S4 waves impacting the transducer. This "common" signal now has two functionalities.

The first of these functionalities involves the delivery of this varying voltage signal to the wave generator over signal line 36. The effect of this delivery is to perform, in a negative feedback manner, real-time, voltage-variation-following adjustments, up and down, in the operating frequency $f_{op}$ of the wave generator in an attempt to maintain the relative point of intersection between line segment 44a and dashed line 46 exactly as shown in FIG. 2, no matter in what lateral direction resonance curve 44 shifts as a consequence of changes occurring in the natural resonance frequency of transducer 14 as determined by the now time-varying, transducer-impacting, anatomical, acoustical wave information (i.e., the "impacting" heart-sound information).

The second functionality involves the effect(s) of what is commonly delivered via signal line 40 to utility output block 26. More specifically, line 40 supplies to block 26 the same time-varying voltage signal which is directly reflective of acoustic information impacting transducer 14. Block 26, as determined freely by the user of this invention, provides a desired utility output which might take the form of a direct display of heart-sound wave forms, a display of numeric and/or text data relating to these waveforms, a control signal, or signals, employable to establish or implement a heart-treatment protocol, such as adjusting/controlling the operation of a pacemaker, and so forth.

The system, the methodology, and their interrelated operations which have just been described will clearly be understood by those skilled in the art to furnish a performance which is distinguished by an extremely high signal-to-noise ratio with respect to gathered acoustical anatomical signals, such as heart-sound signals, accompanied by a large, "effective" sensitivity of transducer 14 regarding such acoustic information.

Turning attention now back briefly to previously mentioned dash-dot-outline block 16a which appears inside the perimeter of transducer block 14 in FIG. 1, block 16a represents a version—a variation—of the invention wherein transducer 14 has been prepared with a fully integrated, i.e., fully mechanically integrated, actuator.

Also as was mentioned earlier, bracket 13 in FIG. 1 represents yet another variation in the implementation of the methodology of the present invention. Specifically, this bracket represents a modified practice wherein what is shown in FIG. 1 is fully embedded within the structure of an anatomically implanted, or implantable, device, such as a pacemaker. In such a modified application, except for the facts that heart-sound signal-gathering activities in terms of transducer vibrating, and of "negative-feedback" adjusting of the stimulating frequency of an actuator, take place entirely within the anatomy, in all other respects, this modification of the invention performs in substantially exactly the same manner which has just been described in conjunction with the described, external methodology application.

The practice of the present invention thus features and involves producing a mechanical disturbance in the natural resonance characteristics of an acoustic transducer—a disturbance which, through the unique application of negative feedback, effectively increases both the signal-to-noise functioning capability, and the effective signal-gathering sensitivity, of that transducer in the practice of gathering heart-sound signals. The fundamental steps of the invention, and relevant, more detailed facets thereof, are expressed in the below-following claims to invention Accordingly, while preferred and best-mode methodology practices, along with certain illustrated and/or suggested variations, have been described herein for improving greatly the signal-to-noise and sensitivity behaviors of an acoustic transducer designed to gather the important, earlier mentioned heart-sounds, we appreciate that other variations and modifications than those specifically mentioned herein may be made without departing from the spirit of the invention.

We claim:

1. A method for acquiring, externally or internally, a subject's anatomical S1, S2, S3, S4 heart-sound information useful in performing a cardio investigation and in producing a related utility output involving that subject comprising placing an acoustic sensor on or within the subject's anatomy at a selected anatomical, the acoustic sensor comprising an acoustical-to-electrical-output transducer specifically having a known, nominal, mechanical resonance frequency which lies within the known range of the S1, S2, S3, S4 heart-sound frequencies, and being capable of providing a sensor electrical output, using a wave generator having a wave generator electrical output, stimulating the transducer at a frequency which is close to its known, nominal, mechanical resonance frequency, coupling to a frequency comparator the electrical outputs of the transducer and of the wave generator, observing over time any time-based differences which exist between the two, thus-compared outputs, interpreting such observed differences as being representations of the subject's S1, S2, S3, S4 heart sounds, and from such interpreted differences, producing a utility output associated with the subject.

2. The method of claim 1, wherein the transducer's mechanical resonance characteristic is representable in a plot of resonance amplitude vs. frequency, which plot essentially frequency-centers nominally on the transducer's mentioned, known, nominal, mechanical resonance frequency, such a plot includes a pair of frequency-spaced, substantially linear plot regions, and said stimulating is performed at a frequency which lies on one of such regions.

3. The method of claim 1, wherein said producing of a utility output involves establishing a treatment protocol for the subject.

4. The method of claim 1 which further comprises furnishing an acoustical-to-electrical transducer and a wave generator which collectively are one of (a) mechanically integrated, and (b) non-integrated, but operatively mechanically in communication with one another during implementation of the method.

5. The method of claim 1, wherein the operation of the mentioned wave generator is a referenced operation, and which further comprises organizing the transducer and the wave generator in a closed, electrical, negative, feedback loop.

* * * * *

UNITED STATES PATENT AND TRADEMARK OFFICE
CERTIFICATE OF CORRECTION

| | | |
|---|---|---|
| PATENT NO. | : 8,348,852 B2 | Page 1 of 1 |
| APPLICATION NO. | : 12/315165 | |
| DATED | : January 8, 2013 | |
| INVENTOR(S) | : Peter T. Bauer et al. | |

It is certified that error appears in the above-identified patent and that said Letters Patent is hereby corrected as shown below:

In the Claims:

Column 8, line 36, "anatomical," should read --anatomical site,--

Signed and Sealed this
Tenth Day of September, 2013

Teresa Stanek Rea
*Acting Director of the United States Patent and Trademark Office*